US011119072B2

(12) United States Patent
Prasad

(10) Patent No.: US 11,119,072 B2
(45) Date of Patent: Sep. 14, 2021

(54) REMOTE, NONINVASIVE, CARDIO-VASCULAR ACTIVITY TRACER AND HARD TARGET EVALUATOR

(71) Applicant: UNITED STATES OF AMERICA AS REPRESENTED BY THE ADMINISTRATOR OF NASA, Washington, DC (US)

(72) Inventor: Narasimha S. Prasad, Yorktown, VA (US)

(73) Assignee: UNITED STATES OF AMERICA AS REPRESENTED BY THE ADMINISTRATOR OF NASA, Washington, DC (US)

( * ) Notice: Subject to any disclaimer, the term of this patent is extended or adjusted under 35 U.S.C. 154(b) by 19 days.

(21) Appl. No.: 16/536,467

(22) Filed: Aug. 9, 2019

(65) Prior Publication Data
US 2020/0049666 A1   Feb. 13, 2020

Related U.S. Application Data

(60) Provisional application No. 62/716,498, filed on Aug. 9, 2018.

(51) Int. Cl.
*G01N 29/24* (2006.01)
*G01N 29/46* (2006.01)
(Continued)

(52) U.S. Cl.
CPC ....... *G01N 29/2418* (2013.01); *A61B 5/0006* (2013.01); *A61B 5/02405* (2013.01);
(Continued)

(58) Field of Classification Search
CPC .... G01N 29/2418; G01N 29/46; G01N 21/39; G01N 21/1702; G01N 21/45;
(Continued)

(56) References Cited

U.S. PATENT DOCUMENTS 4,554,836 A   11/1985   Rudd
4,816,125 A   3/1989    Muller et al.
(Continued)

OTHER PUBLICATIONS

Wang et al., "A New Kind of Laser Microphone for Photoacoustic Applications", Proceedings of the Army Science Conference (26th) Held in Orlando, Florida on Dec. 1-4, 2008.
(Continued)

*Primary Examiner* — Hwa Andrew Lee
(74) *Attorney, Agent, or Firm* — Shawn P. Gorman; Jonathan B. Soike; Helen M. Galus

(57) ABSTRACT

A system for monitoring vibrations in a target region of interest may include a pulsed laser transmitter assembly, interferometric, telescope, and receiver optics, a photo-EMF detector assembly, signal conditioning/processing electronics, and a monitoring circuit/display. The detector assembly, which has a photo-EMF detector and amplifier circuits, generates an output signal indicative of the vibrations. A laser module outputs a source beam at a PRF of at least 2 Hz. A beam splitter device splits the source beam into separate interrogating and reference beams. The mirror directs the reference beam onto the photo-EMF detector for interference with a reflected return signal. The telescope optics generates an amplified return signal, and directs the amplified return signal to the photo-emf detector. The monitoring computer compares the output signal from the signal processor to a baseline to ascertain a difference therebetween, and generates a diagnostic signal indicative of the difference.

18 Claims, 3 Drawing Sheets

(51) Int. Cl.
*G01N 21/39* (2006.01)
*A61B 5/00* (2006.01)
*A61B 5/024* (2006.01)
*G01N 21/17* (2006.01)
*A61B 5/0245* (2006.01)
*G01N 21/45* (2006.01)
*G01N 21/31* (2006.01)
*A61B 5/316* (2021.01)

(52) U.S. Cl.
CPC ......... *G01N 21/1702* (2013.01); *G01N 21/39* (2013.01); *G01N 29/46* (2013.01); *A61B 5/0245* (2013.01); *A61B 5/316* (2021.01); *G01N 21/45* (2013.01); *G01N 2021/1704* (2013.01); *G01N 2021/1761* (2013.01); *G01N 2021/3125* (2013.01); *G01N 2021/3185* (2013.01); *G01N 2201/0221* (2013.01); *G01N 2291/0255* (2013.01)

(58) Field of Classification Search
CPC ... G01N 2021/1761; G01N 2291/0255; G01N 2021/3125; G01N 2201/0221; G01N 2021/3185; G01N 2021/1704; A61B 5/0006; A61B 5/02405; A61B 5/0245; A61B 5/04012; A61B 5/0402; A61B 5/1102; A61B 5/0095; A61B 5/02416
See application file for complete search history.

(56) References Cited

U.S. PATENT DOCUMENTS

| | | | |
|---|---|---|---|
| 4,956,538 A | 9/1990 | Moslehi | |
| 5,883,715 A | 3/1999 | Steinlechner et al. | |
| 6,075,603 A * | 6/2000 | O'Meara | G01D 5/26 356/496 |
| 6,202,470 B1 | 3/2001 | Chou | |
| 6,477,189 B1 | 11/2002 | Takeda | |
| 6,600,564 B1 | 7/2003 | Wang et al. | |
| 7,382,465 B1 | 6/2008 | Pepper | |
| 8,072,609 B1 | 12/2011 | Trivedi et al. | |
| 8,605,262 B2 | 12/2013 | Campbell et al. | |
| 9,995,674 B2 | 6/2018 | Prasad | |
| 2004/0094716 A1 | 5/2004 | Webber | |
| 2007/0115475 A1 | 5/2007 | Shpantzer | |
| 2012/0153119 A1 | 6/2012 | Patil et al. | |
| 2013/0205871 A1 | 8/2013 | Zeninari et al. | |
| 2014/0084395 A1 | 3/2014 | Sparks et al. | |
| 2018/0292309 A1 | 10/2018 | Prasad | |

OTHER PUBLICATIONS

Wang et al., "Non-Contact Cardiac Activity Monitoring using Pulsed Laser Vibrometer", Sensors & Transducers, vol. 162, Issue 1, Jan. 2014, pp. 173-176.

Wang et al., "Biological Life Signs Detection Using High Sensitivity Pulsed Laser Vibrometer", Conference on Lasers and Electro-Optics/Quantum Electronics and Laser Science Conference and Photonic Applications Systems Technologies, OSA Technical Digest Series (CD), Optical Society of America, 2007, paper CWK5.

Wang et al., "Human Life Signs Detection Using High-Sensitivity Pulsed Laser Vibrometer", IEEE Sensors Journal, vol. 7, No. 9, Sep. 2007.

* cited by examiner

REMOTE, NONINVASIVE, CARDIO-VASCULAR ACTIVITY TRACER AND HARD TARGET EVALUATOR

CROSS-REFERENCE TO RELATED PATENT APPLICATION(S)

This patent application claims the benefit of and priority to U.S. Provisional Application Ser. No. 62/716,498, filed on Aug. 9, 2018, the contents of which is hereby incorporated by reference.

STATEMENT REGARDING FEDERALLY SPONSORED RESEARCH OR DEVELOPMENT

The invention described herein was made by an employee of the United States Government and may be manufactured and used by or for the Government of the United States of America for governmental purposes without the payment of any royalties thereon or therefore.

OVERVIEW

Proper cardiac mechanical function requires the heart's chambers, valves, and associated electrical impulses to operate in a concerted manner. Timing errors and inaction of portions of the heart muscle can adversely affect patient health. As a result, techniques and systems have evolved to enable ongoing monitoring of cardiac activity. For instance, the process of electrocardiography, variously abbreviated as ECG and EKG, is commonly used to measure a patient's cardiac electrical activity. With every heartbeat, a corresponding electrical impulse causes the heart muscle to contract. The electrical impulses travel from the upper chambers (atria) to the bottom chambers (ventricles) of the heart muscle, followed by a short period of electrical recovery in which the ventricles return to a resting state. Impulse propagation speed is used to help detect cardiac arrhythmias and other potentially dangerous conditions such as an enlarged or damaged heart muscle, with example arrhythmias including a premature heartbeat, tachycardia (rapid heartbeat), bradycardia (slow heartbeat), atrial fibrillation, atrial flutter, premature ventricular contractions (PVCs), etc.

Certain types of wearable heart monitoring devices such as Holter monitors require attachment of electrode leads to the patient's chest. Leads of other types of wearable monitoring devices are inserted directly into the cardiac muscle. In contrast to such exemplary contact-based and invasive cardiac monitoring devices, non-invasive monitors exist that remotely monitor the heart's activity. One such device is the laser vibrometer, which typically includes an optical microphone arrangement configured to detect minute vibrations using pulsed light and a pressure-sensitive diaphragm. Laser vibrometers may be placed in non-obtrusive locations, such as the patient's fingertips, and used in an unobtrusive way to help monitor heart function. However, existing laser vibrometers remain suboptimal for non-invasive monitoring of cardio-vascular activity and other vibration activity under the particular conditions described herein.

SUMMARY

A remote, non-invasive system is disclosed for monitoring the functionality of a region of interest ("ROI") using reflected laser return signals. The ROI may be a designated surface area of a biological target, for instance, such as a human patient, with the return signals in such an application possibly containing information describing the present cardio-vascular function of the patient. Other ROIs that may be monitored using the present approach include hard targets/non-biological targets, e.g., in the context of non-destructive evaluation ("NDE").

An example application of the present teachings is non-contact/non-invasive monitoring of ongoing mechanical functions of a cardiac muscle, including the opening and closing cycles of the heart's chambers and valves. Such cardiac mechanical activity is detected in a remote, non-contact, non-ionizing manner using a pulsed laser vibrometer specifically optimized using the interferometric setup described herein. The system may be used to improve precision of collected magnitude and timing information of such heart function, and to facilitate the early and accurate detection of certain heart function defects, with the system operating away from the patient's chest cavity and surrounding region while the patient remains clothed. As impulses from a beating heart reverberate through the patient's entire cardio-vascular system, the present method may be used to monitor a patient's ankles, feet, or toes, and/or the neck, back, hands, or another desired ROI.

As a general principle of operation of the disclosed system, it is recognized herein that temporally-phased cardiac pulsations, which in an ideal case ensure proper blood circulation throughout the patient's cardiovascular system, will react act as a force on a patient's garments. The garment material is minutely displaced by the periodic pulsations, with such displacement occurring on the order of nanometers (nm), picometers (pm), or femtometers (fm). The present system is configured to accurately detect the minute displacements in real-time as amplified vibration signals. Other sources of periodic motion causing similar vibration patterns and displacements to occur may be closely tracked and analyzed using the present approach, e.g., the above-noted NDE of hard targets or other non-biological ROIs such as but not limited to fuselages and wings of an example aircraft or spacecraft, and therefore non-invasive/non-contact cardio-vascular monitoring is just one possible beneficial application of the present teachings.

As will be appreciated by one of ordinary skill in the art, cardiac misfunction such as irregular valve timing can produce transient backflow of blood in the patient's circulatory system, which in turn can slow the patient's heartbeat. The resulting vibrations from the slowed heartbeat are relatively weak, particularly in extremities such as the patient's feet and hands. Weakness of this type is possibly indicative of a latent diabetic condition, circulation issue, or other latent problem. The patient may or may not experience cardiac misfunction during the course of a given monitoring period, and therefore the disclosed system may also be used to advantage when monitoring healthy subjects for subtle change, i.e., "patient" does not necessarily imply a degraded state of health. For instance, cardiac, respiratory, or other periodic motion-causing biological functions of the patient may be remotely monitored using the present system while the patient works in a challenging environment, such as in higher temperature, reduced-oxygen, or microgravity environments.

The system according to an example embodiment includes a pulsed laser transmitter and a photo-electromotive force ("photo-EMF") detector arranged with respect to a monitored region of interest ("ROI") using an interferometric setup, with the collective system forming a highly sensitive photo-EMF pulsed laser vibrometer. The disclosed system may be optionally miniaturized as set forth herein into a handheld cardiac monitoring system to facilitate use of the present teachings in a wide range of applications.

The laser transmitter outputs a pulsed or modulated beam at a fixed or tunable wavelength satisfying a predetermined, application-specific detection bandwidth of the photo-EMF detector, and vice versa. The laser transmitter according to an exemplary embodiment has a pulse repetition frequency ("PRF") of at least 2 Hz, e.g., about 10 Hz or higher in some embodiments. As will be appreciated by those of ordinary skill in the art, PRF is the number of laser pulses per unit of time that are output by the laser transmitter. A higher PRF provides higher average output power. Shorter pulse widths provide high peak power levels. Together, both parameters can be used to optimize and/or enhance the signal-to-noise ratio ("SNR").

The laser transmitter in various embodiments may be a solid-state, semiconductor-based, quantum cascade, quantum dot, Raman, or hybrid laser. The laser transmitter may optionally include a microchip laser driven by nonlinear optics. Alternatively, the laser transmitter may include a nonlinear optics-based source, such as an optical parametric oscillator, a harmonic generator, or an optical parametric generator.

The photo-EMF output generated due to vibrations may be further amplified using a highly-sensitive transimpedance operational amplifier to provide optimum impedance matching with the photo-EMF detector. In an optional embodiment, a programmable gain transimpedance amplifier could be used to reduce noise and maintain high bandwidth and high accuracy.

Within the disclosed system, the photo-EMF detector provides motion detection of minute displacements down to about 1 pm or less. The photo-EMF detector generates an output only in response to movement of interference fringes formed on the surface. A vibrating target creates motion of such a fringe pattern and hence a corresponding electrical output is generated. A speckle-tolerant process may be used to allow data to be collected from conformal and rough target surfaces, such as the clothing covering a patient's extremities. Speckle tolerance, as will be appreciated, eliminates the need for ECG-like surface preparation of the patient's skin in applications in which the ROI is a part of a patient's body.

The interferometric setup may be optionally embodied as a relaxed Mach-Zehnder interferometer, with an angle between a reference laser beam and a reflected laser beam from the patient or other target being greater than 0°, e.g., not exceeding 1-2°, for example. An optical path difference condition or spatially-adaptive interferometer scheme between the two laser beams falling incident on an active surface of the photo-EMF detector is similarly relaxed to achieve maximum sensitivity and SNR. Similarly, optimal sensitivity may be realized in the disclosed system using fixed-focus, auto-focus, or variable-focus front end optics closely matched to the wavelength of the laser transmitter.

In a disclosed embodiment, a system for monitoring vibrations in a region of interest of a monitored target includes a photo-EMF detector assembly having a photo-EMF detector and an amplifier circuit. The detector assembly is configured to generate an output signal indicative of the vibrations. The system also includes a pulsed laser assembly having a laser generator configured to output a source beam at a pulse repetition frequency of at least 2 Hz, and a beam splitter device configured to split the source beam into an interrogating beam and a reference beam. A mirror is angled with respect to the pulsed laser system to direct the reference beam onto the photo-EMF detector. Telescope optics are used to optically amplify a return signal reflected from the region of interest to thereby generate an amplified return signal, and to direct the amplified return signal onto the photo-EMF detector to form interferometric fringes.

As part of the disclosed embodiment, a monitoring circuit (e.g., a programmed computer) may receive the output signal from the photo-EMF detector, compare the output signal to a baseline reference to ascertain a difference therebetween, and generate a diagnostic signal indicative of the difference. The photo-EMF detector generates the output signal using information from the reference beam and the amplified return signal.

Also disclosed herein is a method for monitoring vibrations in the region of interest. The method may include generating a source beam at a pulse repetition frequency of at least about 10 Hz using a laser generator of a pulsed laser assembly, and using a beam splitter device to split the source beam into an interrogating beam and a reference beam, and to direct the interrogating beam at the region of interest. The method includes directing the reference beam toward a photo-EMF detector using a mirror angled with respect to the pulsed laser system, and optically amplifying a return signal from the region of interest using telescope optics to thereby generate an amplified return signal. Additionally, the method includes directing the amplified return signal onto the photo-EMF detector and generating, via the photo-EMF detector using information from the reference beam and the amplified return signal, an output signal indicative of the vibrations using the photo-EMF detector and an amplifier circuit, with the output signal being a current caused by motion of the interferometric fringes.

The above summary is not intended to represent every possible embodiment or every aspect of the present disclosure. Rather, the foregoing summary is intended to exemplify some of the novel aspects and features disclosed herein. The above features and advantages, and other features and advantages of the present disclosure, will be readily apparent from the following detailed description of representative embodiments and modes for carrying out the present disclosure when taken in connection with the accompanying drawings and the appended claims.

Figure 1:
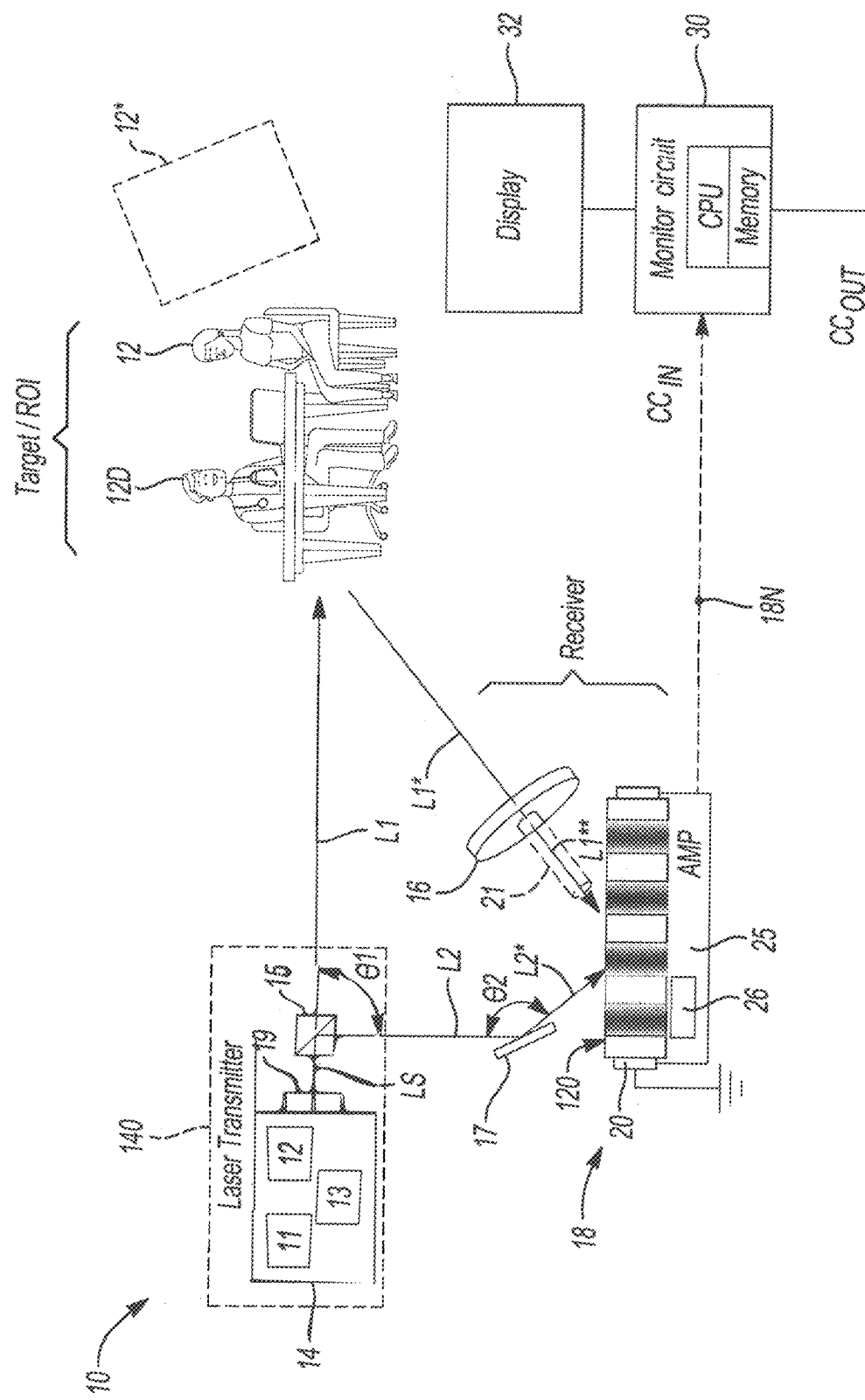
FIG. 1 is a schematic illustration of a remote, non-invasive monitoring system for a region of interest ("ROI") as disclosed herein.

The present disclosure is susceptible to modifications and alternative forms, with representative embodiments shown by way of example in the drawings and described in detail below. Inventive aspects of this disclosure are not limited to the disclosed embodiments. Rather, the present disclosure is intended to cover modifications, equivalents, combinations, and alternatives falling within the scope of the disclosure as defined by the appended claims.

DETAILED DESCRIPTION

For purposes of description herein, the terms "upper," "lower," "right," "left," "rear," "front," "vertical," "horizontal," and derivatives thereof shall relate to the invention as oriented in FIG. 1. However, it is to be understood that the invention may assume various alternative orientations and step sequences, except where expressly specified to the contrary. It is also to be understood that the specific devices and processes illustrated in the attached drawings, and described in the following specification, are simply exemplary embodiments of the inventive concepts defined in the appended claims. Specific dimensions and other physical characteristics relating to the embodiments disclosed herein are not to be considered as limiting, unless the claims expressly state otherwise.

Referring to the drawings, wherein like reference numbers refer to the same or like components in the several Figures, a monitoring system 10 is disclosed herein that is configured to remotely and non-invasively monitor a target or region of interest ("Target/ROI") of a biological target 12 such as a human patient, shown consulting with a physician 12D, or a hard target 12* such as a structural element such as a panel of a vehicle, bridge, building, or other non-biologic object. The monitoring system 10 is configured to operate as a photo-electromotive force ("photo-EMF") pulsed laser-based vibrometer that accurately measures, reports, and potentially acts responsive to extremely minute surface vibrations of the monitored target 12 or 12*.

Enabling technology for the depicted interferometric setup of FIG. 1 is a highly-sensitive photo-EMF detector that generates current due to interferometric fringe motion, which in turn is caused as a consequence of induced vibrations from the target 12 or 12* onto a return signal as described below. When the present interferometric setup used for optional cardio-vascular monitoring of the patient 12, a non-intrusive, non-contact, and highly portable or handheld alternative is provided to the types of ECG/EKG monitors and other cardiac monitoring devices described above. While cardiac monitoring is described herein as a representative application of the present teachings, those of ordinary skill in the art will appreciate that other biological functions such as respiratory function also produce periodic motion, and therefore the source of the vibrations or displacements as measured herein may differ from that of the exemplary heartbeat scenario. Likewise, while a human is depicted as the patient 12, other biological targets may be monitored by the monitoring system 10, such as livestock or other animals, as well as non-living hard targets 12* capable of vibrating or responding to an input force by vibrating. For illustrative consistency, the monitored target will be described hereinafter as a biological target in the form of a human patient, i.e., a patient 12, with example applications of hard target 12* described separately below.

In the present application, the monitoring system 10 may be used to detect minute displacements, e.g., of clothing, blankets, or other garments or covering worn by or draped over the patient 12. Such garments are interposed between an interrogating laser beam (L1) and a designated ROI of the patient 12. As used herein, the term "minute displacements" refers to vertical motion or vibration with magnitudes measured on the picometer or femtometer scale. The monitoring system 10 of FIG. 1 is configured to function through one or more intervening garment layers, and thus the need for surface preparation of the patient's skin is eliminated.

The monitoring system 10 depicted schematically in FIG. 1 includes a pulsed laser system 140 and a photo-EMF detector assembly 18. The pulsed laser system 140 may be implemented using various pulsed laser system arrangements known in the art. In one or more implementations, the pulsed laser system 140 may include a laser transmitter 14 having a laser generator 11, beam control optics 12, and a power supply 13 inclusive of electronics drivers for the beam control optics 12. In one or more embodiments, the photo-EMF detector assembly 18 may include a photo-EMF detector 20 and a transimpedance amplifier (AMP) 25. The transimpedance amplifier 25 in turn includes an embedded programmable gain amplifier 26 that provides a maximum gain-bandwidth under high noise conditions or very low return signal conditions.

The pulsed laser system 140 may also include a beam splitter 15. In general, the laser generator 11 outputs a source laser beam LS at a calibrated frequency and wavelength. The source laser beam LS is directed toward the beam splitter 15, which splits the incident source laser beam LS into constituent beams L1 and L2, the paths for which are either free-space or fiber optically guided in different embodiments. The respective beams L1 and L2 are oriented at a beam angle $\theta1$ with respect to each other, with beam L1 forming the above-noted interrogating beam. For instance, the beam angle $\theta1$ may be 90° such that beam L1 continues along the axis of the source beam LS toward the patient 12 and laser beam L2 is directed toward a reflective mirror 17.

The mirror 17 is oriented at an angle $\theta2$ with respect to the second laser beam L2, e.g., about 110°-135° in the illustrated example embodiment. The photo-EMF detector 20 is arranged with respect to the patient 12 and the mirror 17 such that a mirror-reflected laser beam L2* from the mirror 17 and target-reflected return signals L1* from the patient 12, focused via telescope optics 16 as described below, fall incident upon an active surface 120 of the photo-EMF detector 20.

The laser generator 11 may be variously embodied as a pulsed or modulated laser device, e.g., a solid-state, semiconductor-based, quantum dot, quantum cascade, Rama, or hybrid, Q-switched or mode-locked laser. A passively Q-switched micro-chip laser may be used in some embodiments of the laser generator 11 to provide significant reduction in size, weight, and power consumption. The laser generator 11 may be optionally embodied as a pulsed microchip laser driven by nonlinear optics, e.g., a high-repetition rate, short pulse width, low pulse energy solid-state laser diode. Alternatively, the laser generator 11 may be embodied as a nonlinear optics-based source, such as an optical parametric oscillator, a harmonic generator, or an optical parametric generator. The laser generator 11 may have a fixed or a tunable wavelength satisfying a predetermined detection bandwidth of the photo-EMF detector 20, and vice versa.

Instead of a pulsed laser, in some embodiments the laser generator 11 may be implemented as a continuous wave (CW) laser along with pseudo-random noise (PRN) code for signal correlation and other statistical signal analysis to help in signal acquisition and ranging, e.g., by penetrating deeper into body layers of the patient 12, without being completely obstructed by intervening media such as tissues and ligaments. As will be appreciated by those of ordinary skill in the art, PRN codes may be generated via a number of laser beam modulation techniques. An example of such a technique is described in U.S. Pat. No. 8,605,262 to Campbell et al., which is hereby incorporated by reference. Providing the laser generator 11 with two or more laser beams of with judiciously-separated/sufficiently different wavelengths would result in differential absorption and/or scattering. This feature could provide enhanced vibration SNR or information content of return signals from the ROI, i.e., the target-reflected return signals L1*. Such a technique may be used to in the art of differential absorption or scattering vibrometers, and is akin to differential absorption-based LIDAR techniques.

The laser generator 11 of FIG. 1 further has a pulse repetition frequency ("PRF") of about 2 Hz or higher, e.g., at least about 10 Hz in a possible embodiment. As will be appreciated, the term "PRF" describes the number of laser pulses emitted per unit time, with a higher PRF providing a higher average power, and shorter pulse-widths providing higher peak power levels. Hence, an increased signal-to-noise ratio (SNR) is provided. In a practical setup, a higher-frequency PRF, e.g., several KHz to MHz or more, may be utilized to increase detection sensitivity and SNR.

The laser generator 11 emits the source laser beam LS as a pulsed or a modulated light train. The wavelength of the source laser beam LS may be fixed or tunable in different embodiments. After the source beam LS is split into respective interrogating and reference beams L1 and L2 via the beam splitter 15, the beam L1 acts as a probe/interrogating light beam that is directed toward the patient 12. The beam L2 forms a reference light beam. The telescope assembly 16 collectively represents one or more optics used to collect, project, and/or focus the target-reflected return signals L1* onto the active surface 120 of the photo-EMF detector 20, which is configured to generate a photocurrent to the downstream amplifier circuit 25 whenever optical fringe patterns falling onto the active surface 120 exhibits minute motion, as will be appreciated.

The photo-EMF detector 20 may be single or multi-pixel. In the multi-pixel case, multiple detector pixels could be arranged in a two-dimensional format including simple rectangular configuration similar to a Charged Coupled Device (CCD) or Focal Plane Array (FPA) cameras. Such a multi-pixel embodiment of the photo-EMF detector 20 would help in capturing vibration images without the need for integrated scanners.

Currently, vanadium-doped Cadmium Telluride (CdTe:V) are used to fabricate sensitive photo-EMF detectors. To shift the band edge and extend the cut-off frequencies relative to state-of-the-art detectors of such a type, it is proposed herein to independently dope the CdTe material with Titanium and Chromium, with or without Vanadium in various different embodiments. Bandgap engineering with various dopant concentrations may be used to enhance the utility of current photo-EMF detectors to other laser wavelengths especially to eye-safe wavelengths of greater than 1.5 microns, and also would accommodate higher cutoff frequencies, e.g., from one MHz to tens of MHz or more.

Within the pulsed laser system 140 of FIG. 1, an optical scanner 19 may be attached to or integrated with the front end to the pulsed laser system 140, and is thus located in the path of the source laser beam LS to provide rapid scans over the ROI and thereby generate a "vibration map". The optical scanner 19 is configured with a sufficiently high scan rate (e.g., several kHz or more) in combination with a laser generator 11 having a high PRF, e.g., on the order of several KHz, MHz, or more, and with high bandwidth receiver electronics. Such a setup has the potential to produce images of flow characteristics of minute vibrations through various media and channels of the patient 12, such as nerves, blood vessels, etc. The generated images with distributed spatial and temporal flow characteristics could be generated in real-time or in quasi real-time, limited only by available computer processing speeds.

The optical scanner 19 of FIG. 1 could be mechanical, electro-optical, acousto-optical, liquid crystal based, thin film or similar types that satisfy scan efficiency, throughput, size, volume, weight, and power consumption. The vibration maps of the heart region or any other ROI could help in diagnosing abnormal conditions.

Beam control or variable focus optics may be coupled to the laser head to provide the agility to spatially shape the source beam LS to maximize the return signal, i.e., the target-reflected return signals L1*. The source beam LS could produce a laser output that is collimated, tightly focused, with an application-specific long depth of field, or with divergent beams to cover more surface area in the ROI. Optical elements such as the telescope optics 16 could be either fabricated using various optical components known in the art including but not limited to bulk optics or liquid crystal optics.

The reflected/return laser signals from the patient 12 are converted into corresponding electrical signals by operation of the photo-EMF detector 20 and the amplifier circuit 25, with together along with the telescope optics 16 are labeled "Receiver" in FIG. 1. Weak return signals, i.e., the target-reflected return signals L1*, from the patient 12 could be amplified using an optical amplifier resident within the telescope optics 16, such as a rigid resonant cavity consisting of any combination of lenses, e.g., bulk or liquid crystal or similar, with various curvatures (plane parallel, concave, or convex), with or without a gain medium. Instead of a resonant cavity, a semiconductor amplifier, optical amplifiers based nonlinear optics techniques such as a Raman amplifier, and optical parametric amplifier could be used.

In some embodiments, an optical fiber 21 may be used to connect the telescope assembly 16 to entrance optics of the photo-EMF detector 20. In some implementations such an optical fiber 21 may be configured to be an active optical element and thereby serve as an optical amplifier, outputting an amplified return signal L1**. The geometry of the optical fiber 21 may be long and flexible or short and rigid in various different configurations. In some embodiments, the optical fiber 21 may include one or more core and cladding layers each doped with suitable rare earth ions for pumping via an external optical source (not shown) so as to amplify a specific laser wavelength. The optical fiber 21 could be linear or tapered geometry to optimize guiding, beam focusing, and amplification processes.

The amplifier circuit 25 shown in FIG. 1 may be embodied as amplifier electronics in the form of highly-sensitive transimpedance amplifier and post-amplifier electronics. The interferometric setup of FIG. 1 may be optionally embodied as a relaxed Mach-Zehnder interferometer to determine in relative phase shift and other laser radiation characteristics, as will be appreciated by those of ordinary skill in the art, with angle θ1 between the reference beam/laser beam L2* and the target-reflected return signals L1* being greater than 0°. An optical path difference condition ("spatially-adaptive interferometer scheme") between L1* and L2* is similarly relaxed so as to achieve maximum sensitivity and maximum signal-to-noise ratio (SNR). Similarly, optimal sensitivity may be realized in the disclosed system using fixed-focus, auto-focus, or variable-focus front end optics, embodied as the telescope optics 16, matched to the wavelength of the laser generator 11. Thus, back-scattered radiation from the patient 12 is homodyned with the reference beam L2 in the illustrated example interferometric setup.

As noted above, the photo-EMF detector 20 generates a photocurrent if interferometric fringes incident on the photo-EMF detector 20 experience motion due to vibration of a surface proximate the patient 12, such as a pant leg, sock, blanket, work uniform, spacesuit, or other fabric or textile covering the skin of the patient 12. The photo-EMF detector 20 may generate an output signal indicative of the detected vibrations using information from the reference beam L2 and the amplified return signal L1**, as captured by the interferometric fringes.

Detected signals may be optionally amplified via the amplifier circuit 25 to provide optimum impedance matching with the photo-EMF detector 20. The photo-EMF detector 20 provides motion detection of displacements down to about 1 pm or less. Speckle tolerance capability allows data to be collected from conformal and rough target surfaces, such as garments. As noted above, this capability eliminates the need for ECG-like surface preparation. The target vibration characteristics reduces the speckle noise.

Also shown in FIG. 1 is a monitoring circuit 30 and a display screen ("Display") 32 collectively forming a monitoring computer. The monitoring circuit 30 may be embodied as one or more computer devices having a central processing unit (CPU) and application-sufficient amounts and types of computer-readable memory. The CPU may include signal processing logic, e.g., data reduction, frequency extraction, and post-analysis electronics. The memory may include tangible, non-transitory memory, read only memory in the form of optical, magnetic, or flash memory, random-access memory, electrically-erasable programmable read only memory, etc. The monitoring circuit 30 may also include a high-speed clock or oscillator, analog-to-digital/digital-to-analog circuitry, input/output circuitry and devices, and appropriate signal conditioning and buffer circuitry.

The monitoring circuit 30 of the system 10 may receive input signals (arrow $CC_{IN}$), such as but not limited to the photocurrents, the type and power level of the laser generator 11, range to the patient 12, ambient temperature, the makeup of the propagation medium (e.g., air), and/or other factors that may affect the accuracy of received measurements. Operation of the monitoring system 10 may be regulated responsive to the input signals (arrow $CC_{IN}$) by the monitoring circuit 30 via control output signals (arrow $CC_{OUT}$). Data collected from the patient 12 may be displayed via the display screen 32, e.g., to medical or mission control personnel. Optionally, alerts may be generated responsive to detected errors or anomalies in the measurements, with such alerts possibly triggering subsequent actions such as automatic code generation and/or call activation prompting medical personnel to attend to the patient 12. As the detected vibrations are on the picometer or femtometer scale, sensitivity of the system 10 of FIG. 1 is substantially higher than other non-contact sensors, with the accompanying advantage of being non-invasive.

The monitoring system 10 of FIG. 1 may be miniaturized in some embodiments to facilitate portable or handheld applications. For instance, detection electronics for the photo-EMF detector 20 shown in FIG. 1, e.g., the monitoring circuit 30 and/or drive circuits of the laser transmitter 14 or the photo-EMF detector 20, may be integrated into a transmitter head of the laser transmitter 14. The above-described solid-state laser may be replaced with a microchip laser for additional miniaturization. Additionally, integration of small form-factor LCD display for signal presentation and user interface may embody the monitoring circuit 30 and display 32. The display 32 may be part of a smart phone/device or a handheld monitor coupled to a hardware interface operated through an app on such a smart phone, device, or monitor. Data could be transferred to the display 32 in such an embodiment through a cable or wireless (BLUETOOTH) protocol. Such a miniaturized embodiment of the monitoring system 10 eliminates the requirement for an external laptop computer, for instance, and may facilitate reduced dimensions, weight, and electrical power requirements, e.g., less than 10 W.

Figure 2:
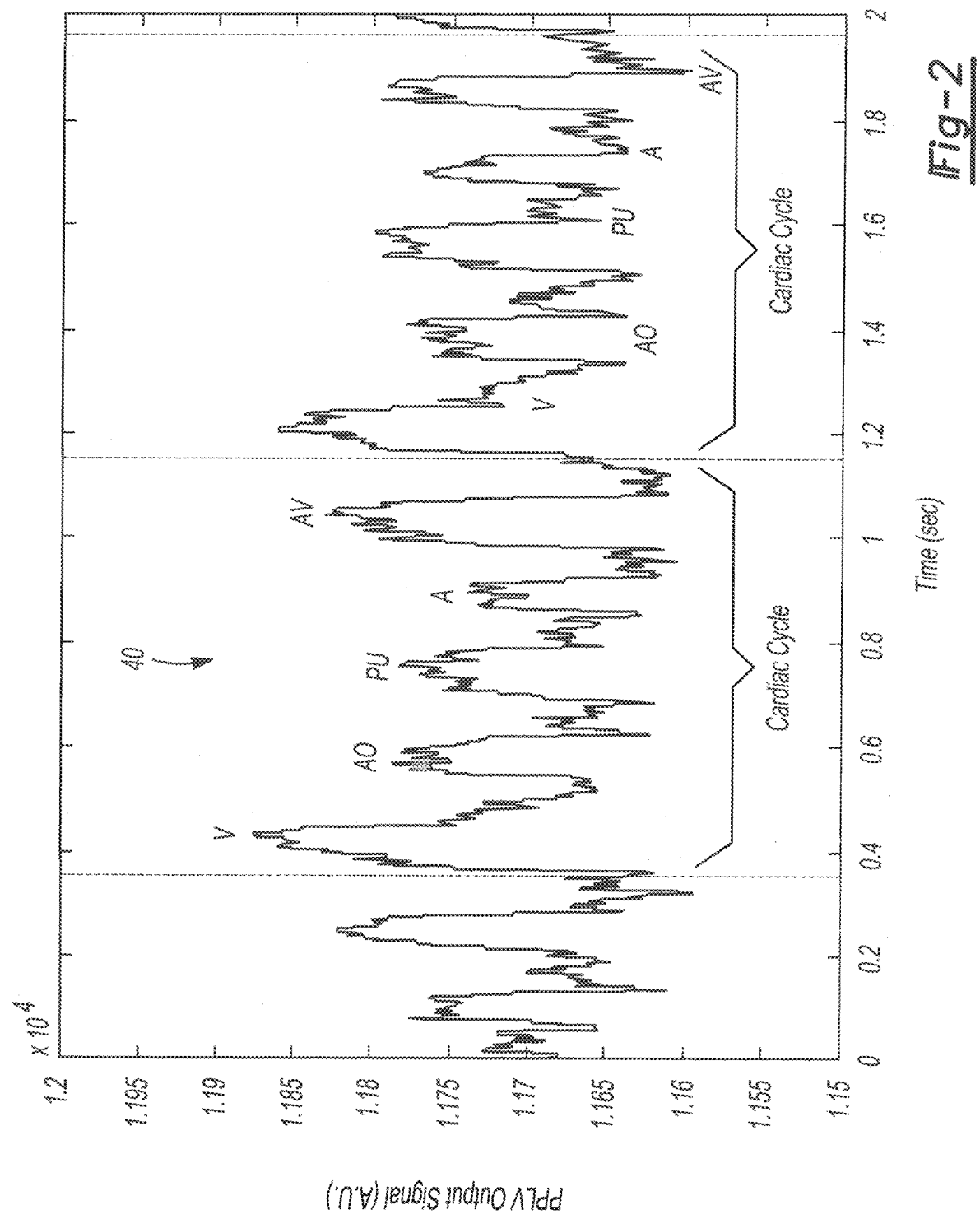
FIG. 2 is a time plot of an output of the system shown in FIG. 1 for a representative interrogation point on a shin area of an example human patient.
Figure 3:
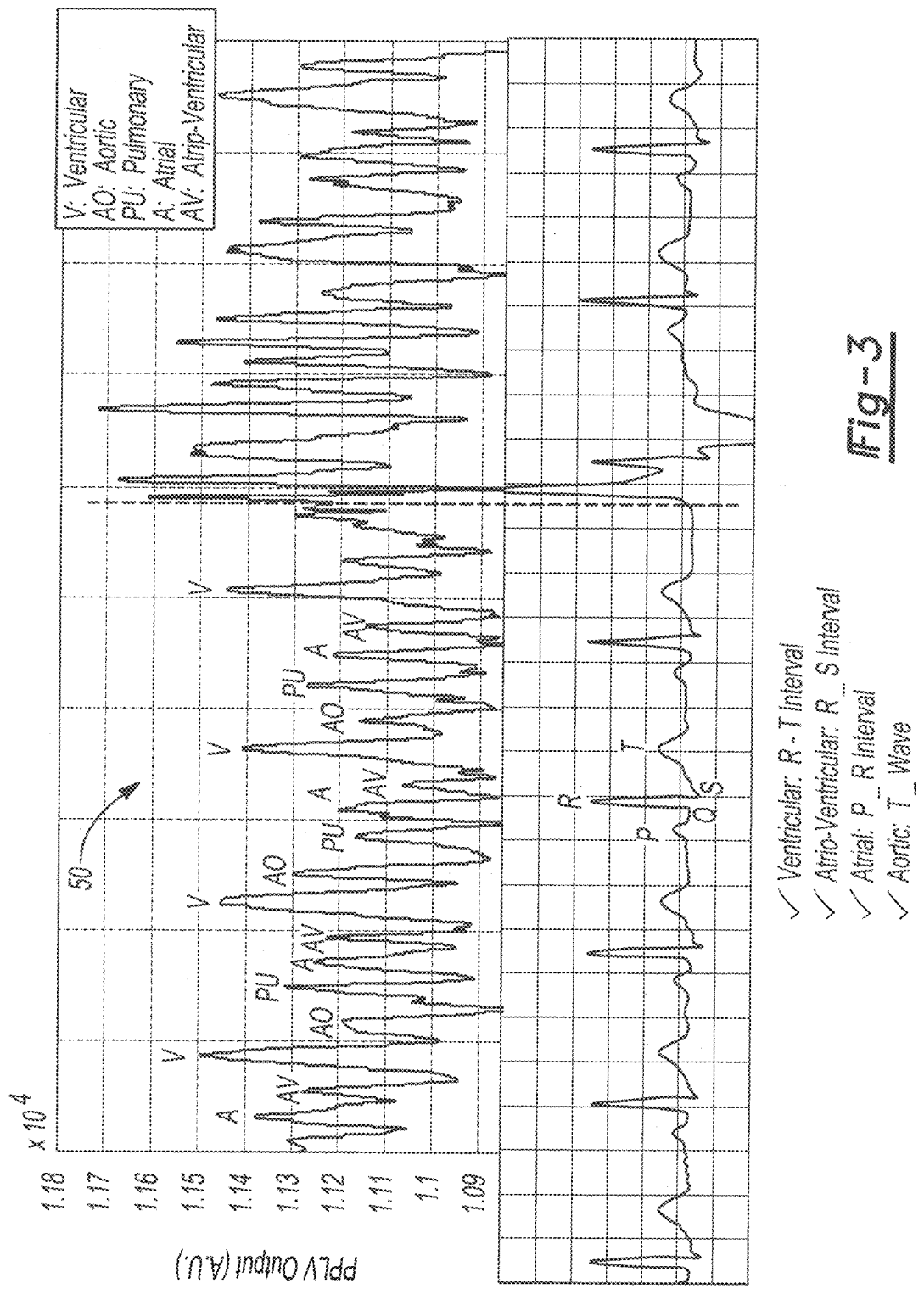
FIG. 3 is a combined time plot of concurrent collection of output of the system of FIG. 1 and a three-lead ECG measurement.

Referring to FIGS. 2 and 3, an example application of the monitoring system 10 of FIG. 1. FIG. 2 shows example cardiac cycles obtained from a shin area of the patient 12, with the shin representing a possible extremity. The patient 12 is clothed, and thus clothing such as a pant leg or a sock is disposed between the monitoring system 10 and the point of interrogation. As depicted, the points on representative trace 40 include ventricular (V), aortic (AO), pulmonary (PU), atrial (A), and atrio-ventricular (AV) activity. A representative cardiac cycle is thus indicated between about t=0.4 to 1.2 seconds (sec) and again from about 1.2 to 2 seconds.

The same nomenclature is used in FIG. 3, which also superimposes a representative concurrent three-lead ECG measurement for comparison. As will be appreciated, ECG signals (trace 60) represent cardiac electrical activity, and are acquired using multiple electrode pads placed in conductive contact with a patient's skin, typically using a conductive gel. Trace 60 is generated by electrical activity toward or away from an electrode, as opposed to measuring specific displacements of clothing as with system 10. The basic ECG waveform consists of three waves: a P wave, a combined QRS wave, and a T wave, with each of the three waves indicating that cardiac electricity has passed through a particular area of the heart muscle and caused contraction to occur. That is, the R-T interval depicts ventricular activity, the R-S interval depicts atrio-ventricular activity, the P-R interval depicts atrial activity, and the T wave depicts aortic activity.

The information contained in the ECG traces 60 may be compared to the more extensive information afforded by traces 40 (FIG. 2) and 50 as generated using the monitoring system 10 of FIG. 1, with the traces 50 corresponding in time to the traces 60 to highlight the more detailed level of information. In traces 50, as with traces 40 of FIG. 2, V represents ventricular activity, AO represents aortic activity, PU represents pulmonary activity, A represents atrial activity, and AV represents atrio-ventricular activity.

The monitoring system 10, being optical in its principle of operation, and thus non-intrusive in its provision of real-time measurements, is uniquely capable of measuring heart valve opening and closing from a location apart from the heart area, doing so when garments are worn by the patient 20. The comparison ECG trace, for instance, provides limited cardiac characteristics by comparison, and is limited relative to the traces 50 by not being a capable of measuring mechanical movements.

Mechanical movements due to heart and other biological functions may be useful in a wide variety of beneficial applications. Outside of hospitals, nursing homes, and rehabilitation facilities, ongoing health monitoring of astronauts, athletes, or other persons operating under constrained environments and/or in bulky clothing such as spacesuits or uniforms may complicate reliable collection of biometric data.

As noted above, the real-time, noncontact optical sensing properties of the monitoring system 10 are beneficial for use in remote cardiac monitoring. Blood circulation carries heartbeat-related vibrations to every part of the body. The vibrations cause minute displacements of clothing, which the monitoring system 10 is adapted to detect and report. It is recognized herein that displacement strength is indicative of vibration strength, which in turn is indicative of the heartbeat in this particular application. Weak vibration at the toes or other extremities may indicate poor circulation and/or a diabetic condition. Thus, the monitoring system 10 may be advantageous to the early detection of diabetes or other diseases by noninvasively monitoring blood circulation at various regions of the body.

Other beneficial applications may be readily envisioned in view of the foregoing disclosure. One possible application involves inducing vibration in the monitored target. For example, an ultrasonic transducer or other probe may be used to inject vibration energy into a monitored target, with the monitoring system 10 of FIG. 1 modified to detect subsurface damage or internal defects based on the resulting vibration signals. Such an approach would expand the present teachings to the realm of non-destructive evaluation (NDE) of various metallic and non-metallic objects, such as but not limited to an aircraft or spacecraft fuselage, wing, panel, engines, or other component in which NDE techniques would be beneficial. In various implementations, induced vibrations can be continuous, pulsed or modulated form of vibrations obtained through a suitable transducer and electronics driver. These vibrationary patterns may be optimally matched with spatial and temporal responses of the target of interest. Changes in vibration amplitudes and frequencies may be extracted and analyzed for abnormalities down to micro or nano-scales.

Example NDE applications include those used to detect latent defects, voids, dislocations, disbonds, discontinuities, micro-cracks or fractures and other inhomogeneities. For the hard targets 12* of FIG. 1, vibrations generated through an external agent (natural or otherwise), such through mechanical impact, natural movements including tectonic plate movement, volcanic eruptions, man-made explosions, etc., would result in various types of surface or bulk propagating waves. A similar analysis of return signals for a region of interest would be carried out for hard targets. The hard targets 12* could be solid parts such as metallic or non-metallic construction, plates (man-made or natural plates such as tectonic), machine parts, aircraft or spacecraft parts, fabrics, earth-related surfaces and plates, etc. The type of waves that would be probed in such example applications may include longitudinal, transverse (shear), surface (Rayleigh), Lamb, Love, Stoneley, Sezawa, and seismic waves (p- and s-) types.

In some embodiments, the disclosed systems for monitoring vibrations may be adapted to perform NDE of live organic matter (e.g., human and/or animal subjects). For example, a pulsed laser vibrometer could be used as an Echocardiagram in conjunction with a source that excites vibrations of a specific region of interest. An external or an internal probe or a catheter fitted with a transducer (e.g., piezoelectric or electromechanical types or micro or nano vibration motors) that is capable of generating controlled vibrations of specific amplitude and frequency may be utilized. The controlled vibrations can be induced on outside surface or inside regions of organs such as through esophagus or intra vascular pathways of a living subject (human or animal). In some applications, the induced vibrations may mimic a synthetic heart generating pulses from a desired region. The induced tiny vibrations are captured by the RENCAT laser vibrometer sensor system whose laser beam is incident on the body surface and the reflected laser beam is be analyzed for changes in vibrational intensity and frequency. In some implementations, detected vibrations are processed to determine frequency shifts resulting from Doppler effect. In some implementations, the internal probe could itself can be fitted with optical fibers with integrated lens system to transmit and receive laser beams.

The induced vibrations themselves could be continuous, pulsed or modulated waveforms to match optimal spatial and temporal nature associated with interrogating regions as well as laser pulse characteristics. Deviations from received vibrational intensity and frequency conforming to attenuation and/or Doppler evaluation from baseline or normally set parametric range would indicate abnormalities and suggest further detailed diagnostics and analysis. The vibration generators could be piezoelectric transducers or other unconventional types that is compatible with form, fit and functionality of the probe. The piezoelectric generators could be micro or nano-scale attached to a suitable electronics driver. They could be configured to be sonotrodes (engineered as a piezoelectric transducer stack).

In one or more embodiments, the systems for monitoring vibrations may be adapted to produce 1-dimensional (1D) data or multi-dimensional (e.g., 2D, 3D, and/or 4D) data from analysis of vibrations detected by laser vibometer. The 2D, 3D, and 4D data may be used to generate images of a specific region. Such vibrational or echo imaging could provide a fast, highly sensitive and cost effective diagnosis.

These and other applications may be readily envisioned by one of ordinary skill in the art in view of the forgoing disclosure. While some of the best modes and other embodiments have been described in detail, various alternative designs and embodiments exist for practicing the present teachings defined in the appended claims. Those skilled in the art will recognize that modifications may be made to the disclosed embodiments without departing from the scope of the present disclosure. Moreover, the present concepts expressly include combinations and sub-combinations of the described elements and features. The detailed description and the drawings are supportive and descriptive of the present teachings, with the scope of the present teachings defined solely by the claims.

What is claimed is:

1. A system for monitoring vibrations in a region of interest of a monitored target, the system comprising:
   a photo-EMF detector assembly having a photo-EMF detector and an amplifier circuit, and configured to generate an output signal indicative of the vibrations, wherein the photo-EMF detector assembly is a multi-pixel device constructed from Cadmium Telluride doped with a combination of transition metals;
   a laser assembly having:
      a laser generator configured to output a source beam; and
      a beam splitter device configured to split the source beam into an interrogating beam and a reference beam;
   a mirror angled with respect to the pulsed laser system to direct the reference beam onto the photo-EMF detector;
   telescope optics configured to amplify a return signal that is reflected from the region of interest to thereby generate an amplified return signal, and to direct the amplified return signal onto the photo-EMF detector to form interferometric fringes; and
   a monitoring circuit configured to receive the output signal from the photo-EMF detector, wherein the output signal is a current caused by motion of the interferometric fringes, compare the output signal to a baseline reference to ascertain a difference there between, and generate a diagnostic signal indicative of the difference;

wherein the photo-EMF detector generates the output signal using information from the reference beam and the amplified return signal.

2. The system of claim 1, wherein the laser assembly is a pulsed laser assembly and the source beam has a pulse repetition frequency of at least 2 Hz.

3. The system of claim 2, wherein the laser generator is a pulsed microchip laser driven by non-linear optics.

4. The system of claim 1, wherein the laser generator has a tunable wavelength and includes an optical parametric oscillator, an optical parametric generator, or a harmonic generator.

5. The system of claim 1, wherein the laser generator includes a continuous wave laser with pseudo-random noise code.

6. The system of claim 1, wherein the combination of transition metals includes Titanium and Chromium.

7. The system of claim 6, wherein the Cadmium Telluride is further doped with Vanadium.

8. The system of claim 1, wherein the pulse repetition frequency is at least 10 Hz.

9. The system of claim 2, wherein the pulsed laser assembly includes an optical scanner located in a path of the source beam, and having an optical scan rate of at least about 2 KHz.

10. The system of claim 9, wherein the optical scanner is one of a mechanical, electro-optical, acousto-optical, liquid crystal, or thin film-based optical scanner.

11. The system of claim 1, further comprising an optical fiber connecting the telescope optics to the photo-EMF detector, wherein the optical fiber is configured to guide the amplified return signal toward the photo-EMF detector.

12. The system of claim 1, wherein the monitored target is a human patient and the region of interest is an area of clothing of the patient.

13. The system of claim 1, wherein the monitored target is a non-biological target, and the region of interest is a surface of the non-biological target.

14. A method for monitoring vibrations in a region of interest of a monitored target, the method comprising:
   generating a source beam at a pulse repetition frequency of at least about 10 Hz using a laser generator of a pulsed laser assembly;
   using a beam splitter device to split the source beam into an interrogating beam and a reference beam, wherein the interrogating beam is directed at the region of interest;
   directing the reference beam toward a photo-EMF detector using a mirror angled with respect to the pulsed laser system;
   optically amplifying a return signal from the region of interest using telescope optics to thereby generate an amplified return signal;
   directing the amplified return signal onto the photo-EMF detector to form interferometric fringes; and
   generating, via the photo-EMF detector using information from the reference beam and the amplified return signal, an output signal indicative of the vibrations using the photo-EMF detector and an amplifier circuit, wherein the output signal is a current caused by motion of the interferometric fringes;
   receiving the output signal from the photo-EMF detector via a monitoring circuit;
   comparing the output signal to a baseline reference, via the monitoring circuit, to thereby ascertain a difference therebetween; and
   generating a diagnostic signal indicative of the difference.

15. The method of claim 14, wherein generating the source beam includes using (i) a pulsed microchip laser driven by non-linear optics, or (ii) a continuous wave laser with pseudo-random noise code.

16. The method of claim 14, wherein the photo-EMF detector assembly is constructed from Cadmium Telluride doped with Titanium and Chromium.

17. The method of claim 14, further comprising using an optical scanner located in a path of the source laser to scan the region of interest.

18. The method of claim 14, further comprising using an optical fiber to guide the amplified return signal toward the photo-EMF detector, and wherein the monitored target is a human patient and the region of interest is an area of clothing of the patient.

* * * * *